(12) United States Patent
Morita

(10) Patent No.: US 8,664,953 B2
(45) Date of Patent: Mar. 4, 2014

(54) MAGNETIC RESONANCE IMAGING APPARATUS SETTING FIELD-OF-VIEW (FOV) BASED ON PATIENT SIZE AND REGION OF INTEREST (ROI)

(75) Inventor: Yoshinari Morita, Tochigi-ken (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 937 days.

(21) Appl. No.: 12/700,977

(22) Filed: Feb. 5, 2010

(65) Prior Publication Data

US 2010/0201360 A1    Aug. 12, 2010

(30) Foreign Application Priority Data

Feb. 10, 2009 (JP) ................................. 2009-029059
Jan. 20, 2010 (JP) ................................. 2010-009962

(51) Int. Cl.
*G01R 33/54* (2006.01)
*A61B 5/055* (2006.01)

(52) U.S. Cl.
USPC .......................................... 324/309; 324/307

(58) Field of Classification Search
USPC .................. 324/300–322; 600/407–435; 382/128–131
See application file for complete search history.

(56) References Cited

U.S. PATENT DOCUMENTS

| | | | |
|---|---|---|---|
| 4,786,871 A | 11/1988 | Hoshino | |
| 6,469,505 B1 * | 10/2002 | Maier et al. | 324/309 |
| 6,828,787 B2 | 12/2004 | Oesingmann | |
| 6,989,673 B2 * | 1/2006 | Zhu | 324/318 |
| 7,053,618 B2 * | 5/2006 | Zhu | 324/318 |
| 7,075,301 B2 * | 7/2006 | Zhu | 324/318 |
| 7,075,302 B2 * | 7/2006 | Zhu | 324/318 |
| 7,385,396 B2 * | 6/2008 | Zhu | 324/309 |
| 7,535,226 B2 * | 5/2009 | Takahashi et al. | 324/309 |
| 7,659,720 B2 * | 2/2010 | Furudate et al. | 324/309 |
| 7,701,214 B2 * | 4/2010 | Kurokawa et al. | 324/318 |
| 7,808,240 B2 * | 10/2010 | Zhu | 324/309 |
| 7,821,267 B2 * | 10/2010 | Yatsui et al. | 324/318 |
| 7,944,206 B2 * | 5/2011 | Frydman et al. | 324/307 |
| 8,008,918 B2 * | 8/2011 | Sugiura | 324/309 |
| 8,536,868 B2 * | 9/2013 | Zenge | 324/307 |
| 2003/0004408 A1 * | 1/2003 | Zhu | 600/410 |
| 2003/0220558 A1 | 11/2003 | Busse | |
| 2005/0110487 A1 * | 5/2005 | Zhu | 324/309 |
| 2005/0110488 A1 * | 5/2005 | Zhu | 324/309 |
| 2005/0134267 A1 * | 6/2005 | Zhu | 324/309 |

(Continued)

FOREIGN PATENT DOCUMENTS

| | | |
|---|---|---|
| JP | 3-16851 B2 | 3/1991 |
| JP | 3-207343 A | 9/1991 |
| JP | 4-276237 A | 10/1992 |

*Primary Examiner* — Melissa Koval
*Assistant Examiner* — Tiffany Fetzner
(74) *Attorney, Agent, or Firm* — Yoshida & Associates, LLC

(57) ABSTRACT

When the settings of the region of interest are received from the operator, the measurement data acquisition control unit performs control so that an image for generating profile data is taken, and the data processing unit generates profile data in the encoding directions of the set region of interest. Then, the field-of-view setting unit sets the field of view in each of the encoding directions, based on the relationship between the dimensions of the subject P in the encoding directions that are calculated from the profile data of the encoding directions and the dimensions of the region of interest in the corresponding encoding directions, by use of coefficients stored in the coefficient storage unit.

20 Claims, 14 Drawing Sheets

(56) References Cited

U.S. PATENT DOCUMENTS

| | | | |
|---|---|---|---|
| 2005/0134268 A1* | 6/2005 | Zhu | 324/309 |
| 2007/0247155 A1* | 10/2007 | Zhu | 324/318 |
| 2008/0111546 A1* | 5/2008 | Takahashi et al. | 324/307 |
| 2008/0180104 A1* | 7/2008 | Furudate | 324/318 |
| 2009/0219020 A1* | 9/2009 | Kurokawa et al. | 324/309 |
| 2009/0273346 A1* | 11/2009 | Zhu | 324/314 |
| 2009/0309595 A1* | 12/2009 | Yatsui | 324/309 |
| 2010/0001727 A1* | 1/2010 | Frydman et al. | 324/310 |
| 2010/0052676 A1* | 3/2010 | Sugiura | 324/309 |
| 2010/0201360 A1* | 8/2010 | Morita | 324/309 |

* cited by examiner

SETTING OF REGION OF INTEREST

IMAGING OF SAME REGION OF SAME SUBJECT

PARALLEL IMAGING

MAGNETIC RESONANCE IMAGING APPARATUS SETTING FIELD-OF-VIEW (FOV) BASED ON PATIENT SIZE AND REGION OF INTEREST (ROI)

CROSS-REFERENCE TO RELATED APPLICATIONS

This application is based upon and claims the benefit of priority from the prior Japanese Patent Application No. 2009-29059, filed on Feb. 10, 2009, and Japanese Patent Application No. 2010-009962, filed on Jan. 20, 2010; the entire contents of both of which are incorporated herein by reference.

BACKGROUND OF THE INVENTION

1. Field of the Invention

The present invention relates to a magnetic resonance imaging apparatus.

2. Description of the Related Art

Conventionally, magnetic resonance imaging apparatuses (hereinafter, "MRI apparatuses") that collect data of the internal body of a subject by use of a magnetic resonance phenomenon and reconstruct a magnetic resonance image of the internal body play an important role in various medical practices such as diagnosis, treatment, and surgery planning of diseases.

With the magnetic resonance imaging method executed by an MRI apparatus, a spatial resolution, an imaging time, and a signal/noise ratio of a magnetic resonance image and the like are dependent on imaging conditions such as the field of view (FOV), the imaging matrix, and the number of acquisition, which are parameters of pulse sequences. For this reason, the MRI apparatus is one of medical instruments that require settings for a large number of imaging conditions.

For example, because the sizes of subjects vary, the operator of the MRI apparatus needs to adjust the region of interest (including a slab if an image to be taken is three-dimensional) in accordance with the size and position of the subject at the time of planning the positioning.

When the region of interest to be set at the time of positioning planning is different from the preset field of view, the operator needs to adjust the field of view in accordance with the size of the subject. For example, when the subject is larger than the field of view but the field of view is not large enough with respect to the region of interest, aliasing artifacts may appear in the magnetic resonance image. Then, the operator needs to adjust the imaging region.

When the region of interest is too small for the subject, an image is taken in a large field of view to reconstruct a magnetic resonance image, and then the region of interest is cut out of the reconstructed magnetic resonance image so that aliasing artifacts can be avoided. With such a method, small sampling intervals in the time domain are set to maintain the spatial resolution, and after a Fourier transform is performed, the region of interest is cut out.

However, if a large field of view is set to prevent aliasing artifacts from occurring in the magnetic resonance image and small sampling intervals are set in the time domain to maintain the spatial resolution in the magnetic resonance image, the imaging time is adversely increased. To prevent the imaging time from unnecessarily increasing, the operator needs to determine the minimum field of view in which no aliasing artifact would enter the region of interest.

On the other hand, when the subject is smaller than the field of view, an aliasing artifact would not appear if the region of interest is used as a field of view. However, the imaging time would be increased because unnecessary areas have to undergo the imaging process. In addition, because the unnecessary areas need to undergo the imaging process, the amount of data would be increased. This would especially increase the load on the system for executing the data collecting process and the reconstruction calculating process. Thus, even when the size of the subject is smaller than the field of view, the operator needs to determine the minimum field of view so that the imaging time would not be unnecessarily increased.

To reduce the imaging time, a technique is known with which a direction in which the projection has the minimum width (the minimum size of the subject) is detected from projection data obtained by projecting the subject from multiple directions, and the detected direction is automatically set as a phase encoding direction (see, for example, JP-A H3-16851 (KOKOKU)).

According to the above conventional technique, the imaging time may be reduced, but the relationship between the sizes of the subject and the region of interest is not taken into consideration. Thus, the operator has to determine the minimum field of view in which aliasing artifacts would not enter the region of interest.

In other words, the operator needs to set the region of interest and also to adjust the minimum field of view at the time of planning the positioning. For this purpose, the accurate position of the region of interest in the subject has to be obtained. This means that it takes a lot of time and efforts for the operator to set the minimum field of view. This setting operation requires a long time to learn. Thus, the total examination time tends to be increased.

As discussed above, a problem of difficulty in setting the field of view free of artifacts resides in the conventional technologies.

SUMMARY OF THE INVENTION

According to an aspect of the present invention, a magnetic resonance imaging apparatus includes an acquiring unit that acquires a dimension of a subject for each of encoding directions set in an region of interest that is received from an operator; and a field-of-view setting unit that sets a field of view for taking a magnetic resonance image, based on a size relationship between the dimension of the subject acquired for each of the encoding directions by the acquiring unit and a dimension of the region of interest for each of the encoding directions.

According to another aspect of the present invention, a magnetic resonance imaging apparatus includes an acquiring unit that acquires the dimension of the subject in each of encoding directions in the region of interest that is received from the operator; and a field-of-view setting unit that sets the field of view, based on the dimension of the subject in each of the encoding directions that is acquired by the acquiring unit and the dimension of the region of interest in each of the encoding directions, to take a magnetic resonance image in which either one of a time resolution and a spatial resolution is given a priority.

According to still another aspect of the present invention, a magnetic resonance imaging apparatus includes an acquiring unit that acquires a dimension of a subject in each of encoding directions set in an region of interest that is received from an operator; a field-of-view setting unit that sets a field of view for taking a magnetic resonance image of the subject, based on the dimension of the subject in each of the encoding directions acquired by the acquiring unit and a dimension of the region of interest in each of the encoding directions; and a display control unit that performs control in such a manner that the field of view set by the field-of-view setting unit is displayed on a certain display unit.

DETAILED DESCRIPTION OF THE PREFERRED EMBODIMENTS

Exemplary examples of the magnetic resonance imaging apparatus according to the present invention are explained below with reference to the attached drawings. Hereinafter, the magnetic resonance imaging apparatus is referred to as an "MRI apparatus".

Figure 1:
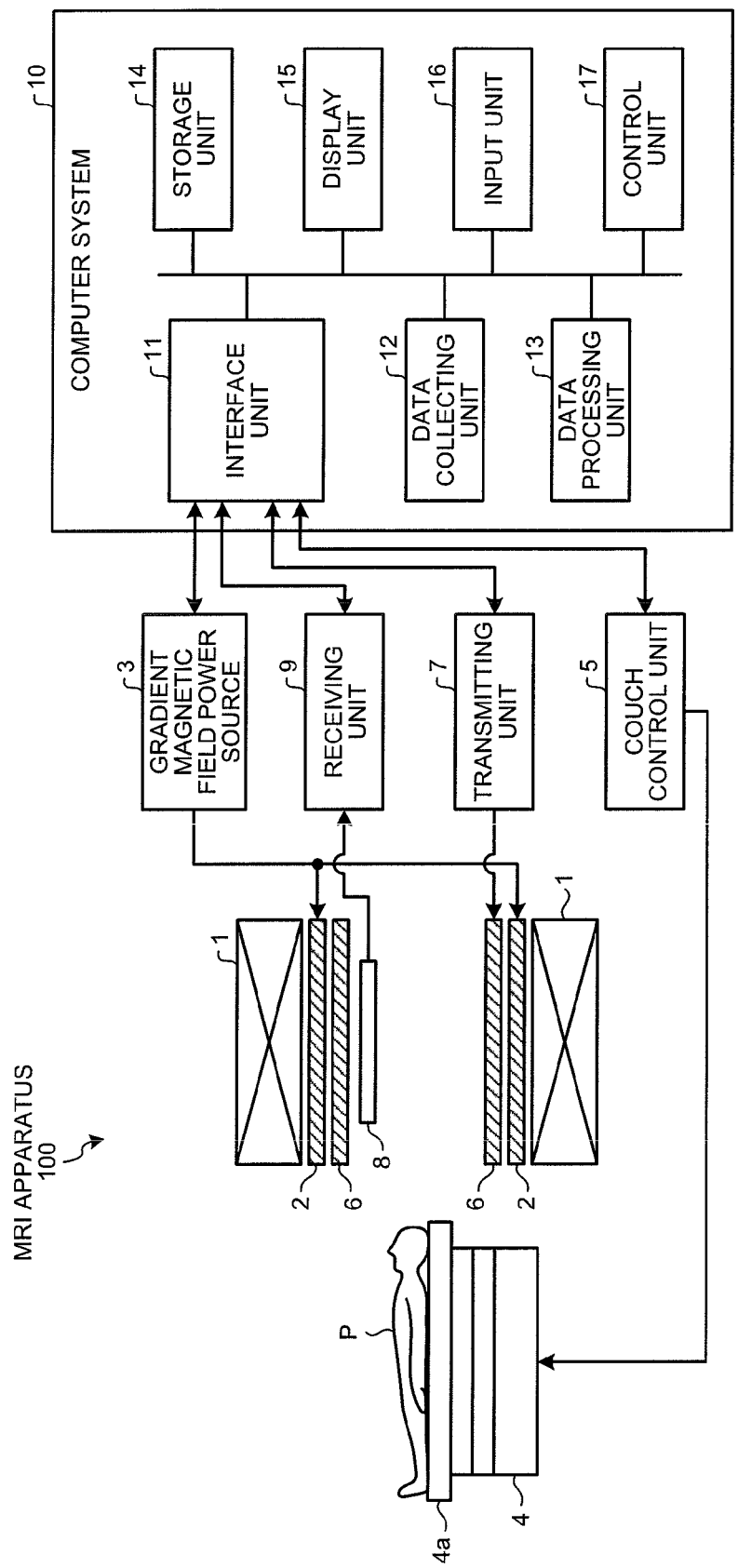
FIG. 1 is a diagram for explaining a configuration of an MRI apparatus according to an embodiment of the present invention.

First, a configuration of an MRI apparatus according to the present embodiment is explained. FIG. 1 is a diagram for explaining a configuration of an MRI apparatus according to an embodiment of the present invention. As shown in FIG. 1, an MRI apparatus 100 according to the present embodiment includes a static magnetic-field magnet 1, a gradient magnetic field coil 2, a gradient magnetic field power source 3, a couch 4, a couch control unit 5, a transmission RF coil 6, a transmitting unit 7, a reception RF coil 8, a receiving unit 9, and a computer system 10.

The static magnetic-field magnet 1 is a hollow, cylindrical magnet that generates a static magnetic-field uniformly in its inside space, and a permanent magnet or a superconducting magnet may be adopted.

The gradient magnetic field coil 2 is a hollow, cylindrical coil and is arranged inside the static magnetic-field magnet 1. The gradient magnetic field coil 2 is formed by combining three coils corresponding to the X, Y, and Z axes that are orthogonal to one another. When the power is individually supplied from the later-described gradient magnetic field power source 3, these three coils generate gradient magnetic fields that can change their magnetic field intensities along the X, Y, and Z axes. The Z axis is the same as the direction of the static magnetic-field.

The gradient magnetic fields generated by the gradient magnetic field coil 2 along the X, Y, and Z axes correspond to, for example, a gradient magnetic field Gs for slice selecting, a gradient magnetic field Ge for phase encoding, and a gradient magnetic field Gr for reading out (frequency encoding). The gradient magnetic field Gs for slice selecting is adopted to determine an arbitrary imaging cross section. The gradient magnetic field Ge for phase encoding is adopted to change the phase of a magnetic resonance signal in accordance with the spatial position. The gradient magnetic field Gr for reading out is adopted to change the frequency of the magnetic resonance signal in accordance with the spatial position.

The gradient magnetic field power source 3 supplies power to the gradient magnetic field coil 2, based on a pulse sequence received from the computer system 10.

The couch 4 is a device that has a top board 4a on which the subject P lies down, and under control by the later-described couch control unit 5, the top board 4a on which the subject P lies down is carried into the hollow (imaging opening) of the gradient magnetic field coil 2. The longitudinal direction of the bed 4 is arranged in parallel with the central axis of the magnetostatic magnet 1.

The couch control unit 5 controls the movement of the couch 4, and drives the couch 4 to carry the top board 4a in the longitudinal direction and in the vertical direction.

The transmission RF coil 6 is arranged inside the gradient magnetic field coil 2, and generates a radio-frequency magnetic field high-frequency magnetic field by a high-frequency pulse supplied by the transmitting unit 7.

The transmitting unit 7 transmits high-frequency pulses corresponding to the Larmor frequency to the transmission RF coil 6, based on the pulse sequence received from the computer system 10, and includes an oscillating unit, a phase selecting unit, a frequency converting unit, an amplitude modulating unit, a radio-frequency power amplifying unit, and the like.

The oscillating unit generates a radio-frequency signal of a resonance frequency unique to a subject nucleus in the static magnetic field. The phase selecting unit selects a phase of the radio-frequency signal. The frequency converting unit converts the frequency of a radio-frequency signal output by the phase selecting unit. The amplitude modulating unit modulates amplitude of a radio-frequency signal output by the frequency converting unit in accordance with, for example, a sinc function. The radio-frequency power amplifying unit amplifies a radio-frequency signal output by the amplitude modulating unit. As a result of operations of the above units, the transmitting unit 7 transmits a radio-frequency pulse corresponding to a Larmor frequency to the transmission RF coil 6.

The reception RF coil 8 is arranged inside the gradient magnetic field coil 2, and receives a magnetic resonance signal radiated from the subject owing to an influence of the radio-frequency magnetic field. When receiving the magnetic resonance signal, the reception RF coil 8 outputs the received magnetic resonance signal to the receiving unit 9.

The receiving unit 9 generates magnetic resonance signal data by converting the frequency and performing analog/digital (A/D) conversion of the magnetic resonance signal output by the reception RF coil 8 in accordance with the pulse sequence received from the computer system 10. The receiving unit 9 transmits the generated magnetic resonance signal data to the computer system 10.

The computer system 10 performs overall control of the MRI apparatus 100, data collection, image reconstruction, and the like. As illustrated in FIG. 1, the computer system 10 includes an interface unit 11, a data collecting unit 12, a data processing unit 13, a storage unit 14, a display unit 15, an input unit 16, and a control unit 17.

The interface unit 11 is a processing unit that is connected to the gradient magnetic field power source 3, the couch control unit 5, the transmitting unit 7, and the receiving unit 9 to control the input and output of signals that are exchanged between the connected units and the computer system 10.

The data collecting unit 12 is a processing unit that collects the magnetic resonance signal data transmitted by the receiving unit 9 by way of the interface unit 11, and also generates k-space data by allocating the collected magnetic resonance signal data in k-space. Then, the data collecting unit 12 stores the k-space data in the storage unit 14.

The data processing unit 13 conducts post-processing, or in other words reconstruction processing such as the Fourier transform onto the k-space data stored in the storage unit 14 to reconstruct image data (magnetic resonance images).

Furthermore, the data processing unit 13 generates profile data in each encoding direction from the magnetic resonance signal data collected in accordance with the high-frequency pulse applied to the subject P. The detailed explanation will be provided later. The encoding directions represent the readout (RO) direction (also referred to as frequency encoding direction) and the phase encoding (PE) direction. When a three-dimensional magnetic resonance image is to be taken, the slice encoding (SE) direction is included in addition to the RO and PE directions.

The storage unit 14 stores therein the k-space data received from the data collecting unit 12, the magnetic resonance image reconstructed by the data processing unit 13, and the like, for each subject P.

The storage unit 14 also stores therein various coefficients used in the process performed by a field-of-view setting unit 17b, which are described later.

The display unit 15 is a monitor such as a cathode ray tube (CRT) display and a liquid crystal display that displays various kinds of information including a magnetic resonance image, under the control performed by the control unit 17.

The input unit 16 includes a pointing devise, such as a mouse and a trackball, and a keyboard to receive various operations and information from the operator. The input unit 16 cooperates with the display unit 15 to provide the operator of the MRI apparatus 100 with a user interface for receiving the operations. For example, the input unit 16 receives information on the region of interest from the operator, who is referring to the positioning image displayed on the display unit 15 at the time of planning the positioning.

The control unit 17 is a processing unit that includes a not-shown CPU and memory, and the like, and controls the entire MRI apparatus 100.

For example, the control unit 17 generates pulse sequence information, based on imaging conditions that are input through the input unit 16 by the operator and the setting field of view, and transmits the generated sequence information to the gradient magnetic field power source 3, the transmitting unit 7, and the receiving unit 9 by way of the interface unit 11, to execute the magnetic resonance image-taking. In addition, the control unit 17 controls the process performed by the data processing unit 13. The control unit 17 also controls screen display on the display unit 15. The control unit 17 will be described later.

Figure 2:
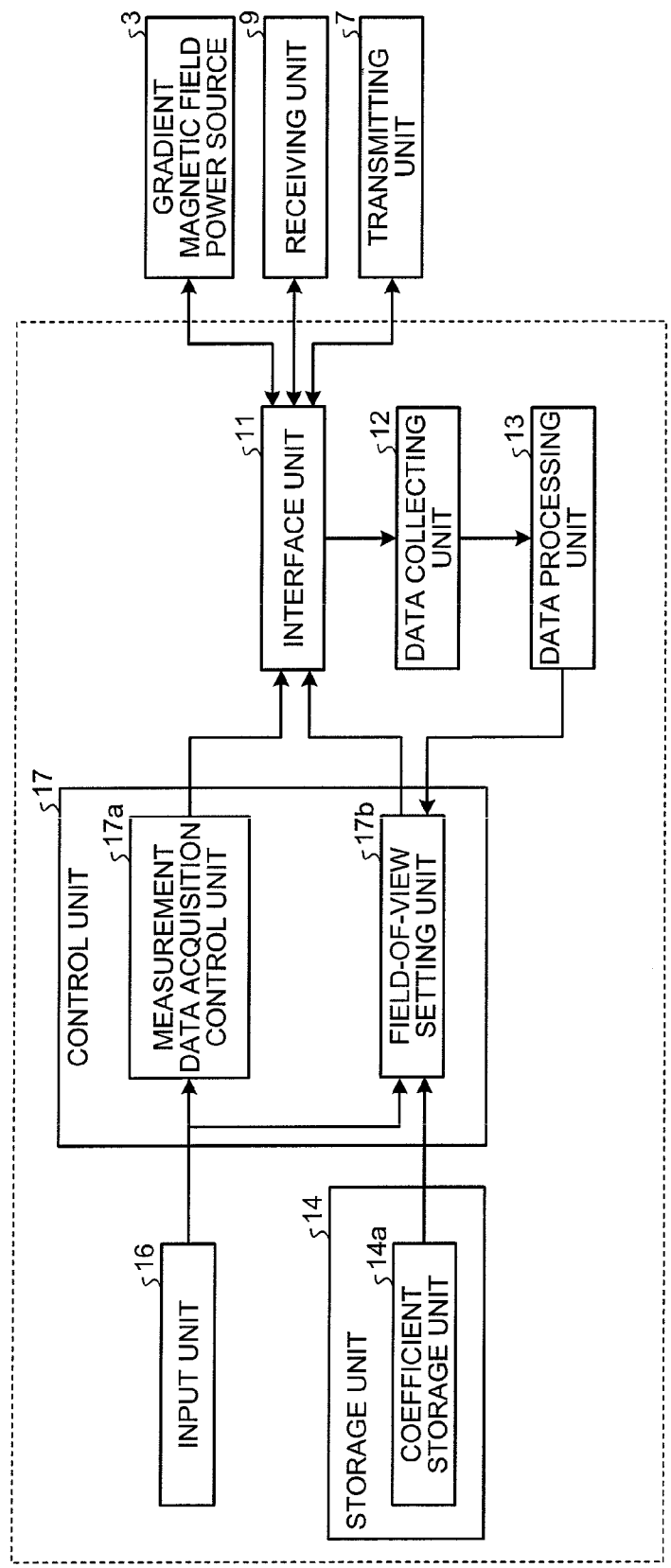
FIG. 2 is a diagram for explaining a configuration of a control unit according to the embodiment.
Figure 3:
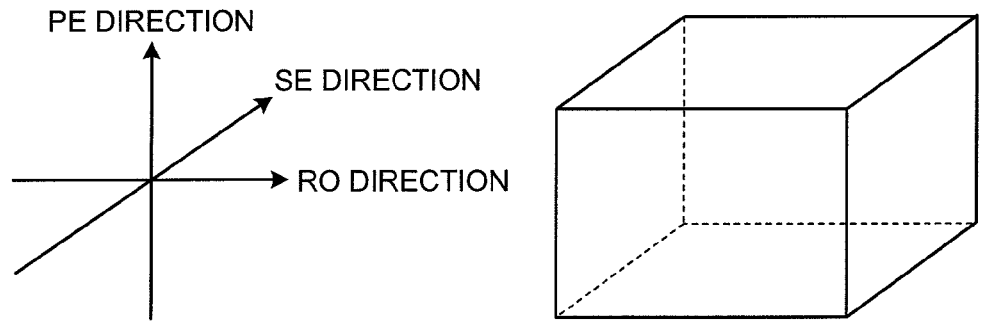
FIG. 3 is a diagram for explaining a region of interest.
Figure 4:
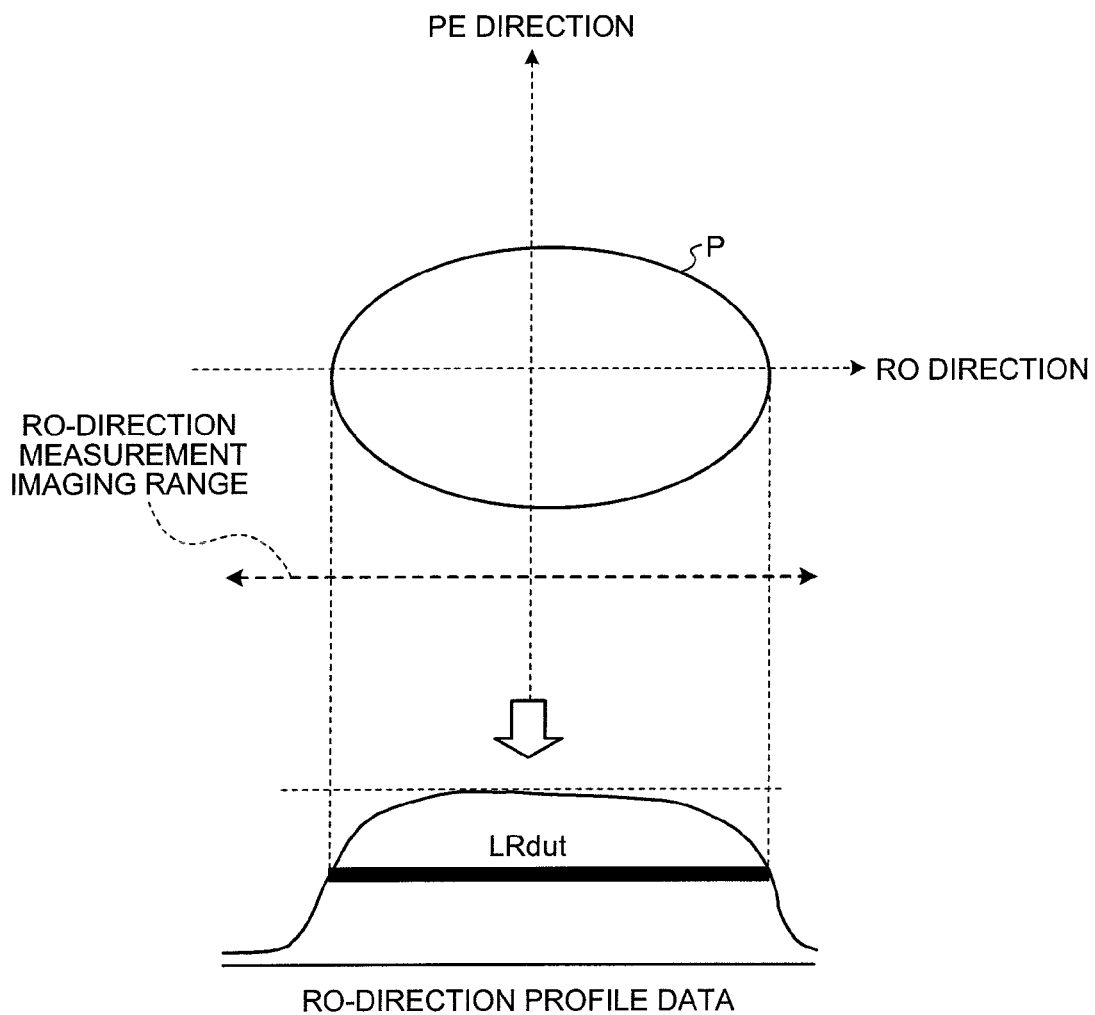
FIGS. 4 to 6 are diagrams for explaining the setting of the field of view in the RO direction.
Figure 5:
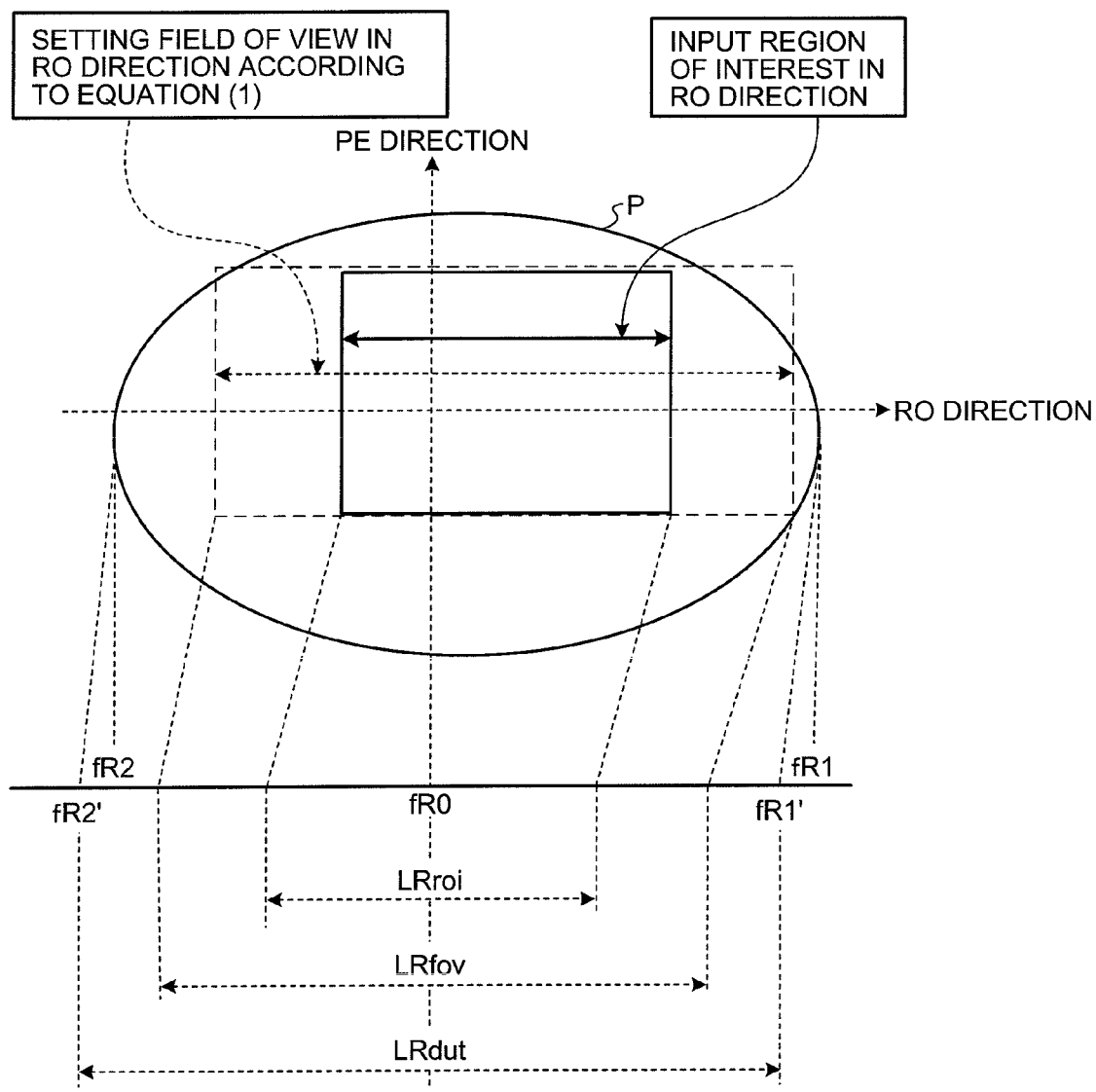
Figure 6:
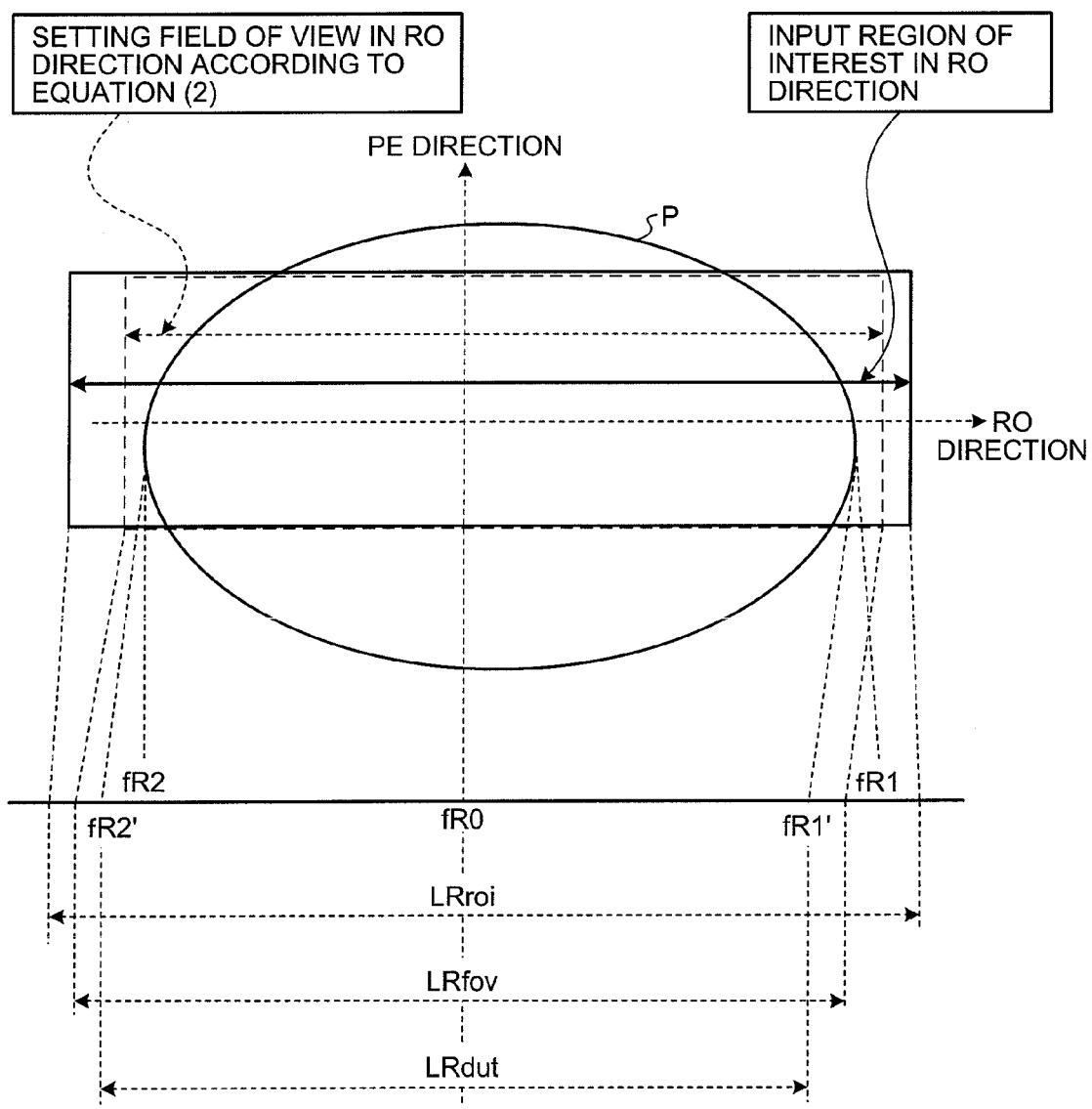
Figure 7:
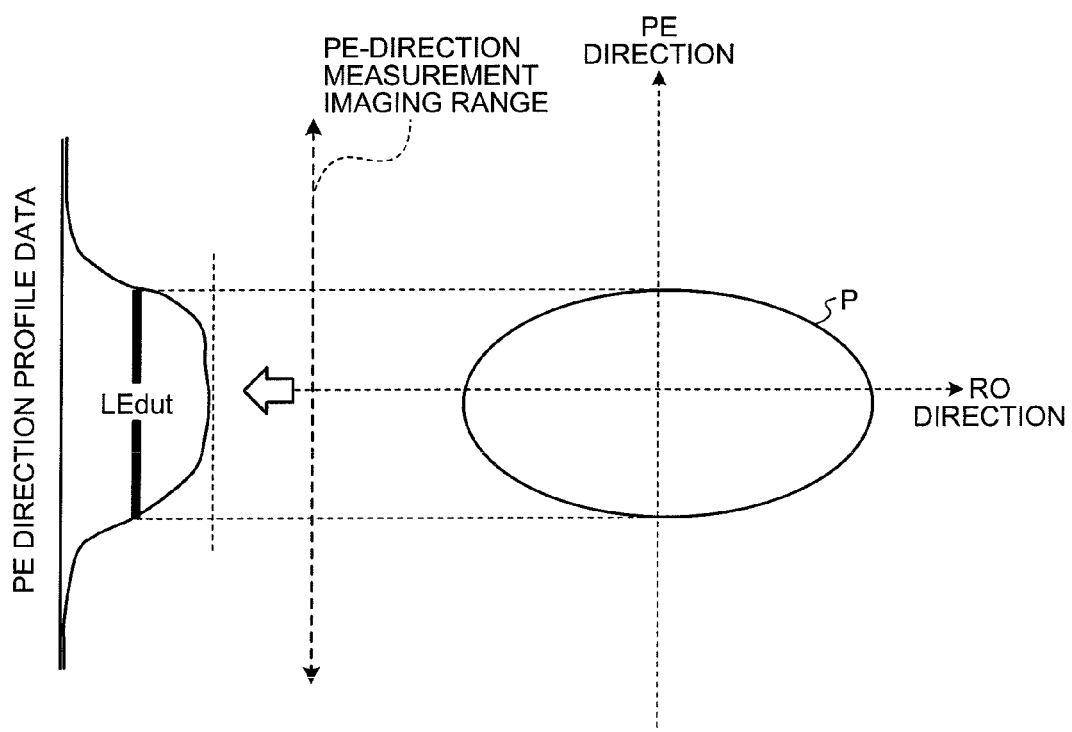
FIGS. 7 to 9 are diagrams for explaining the setting of the field of view in the PE direction.
Figure 8:
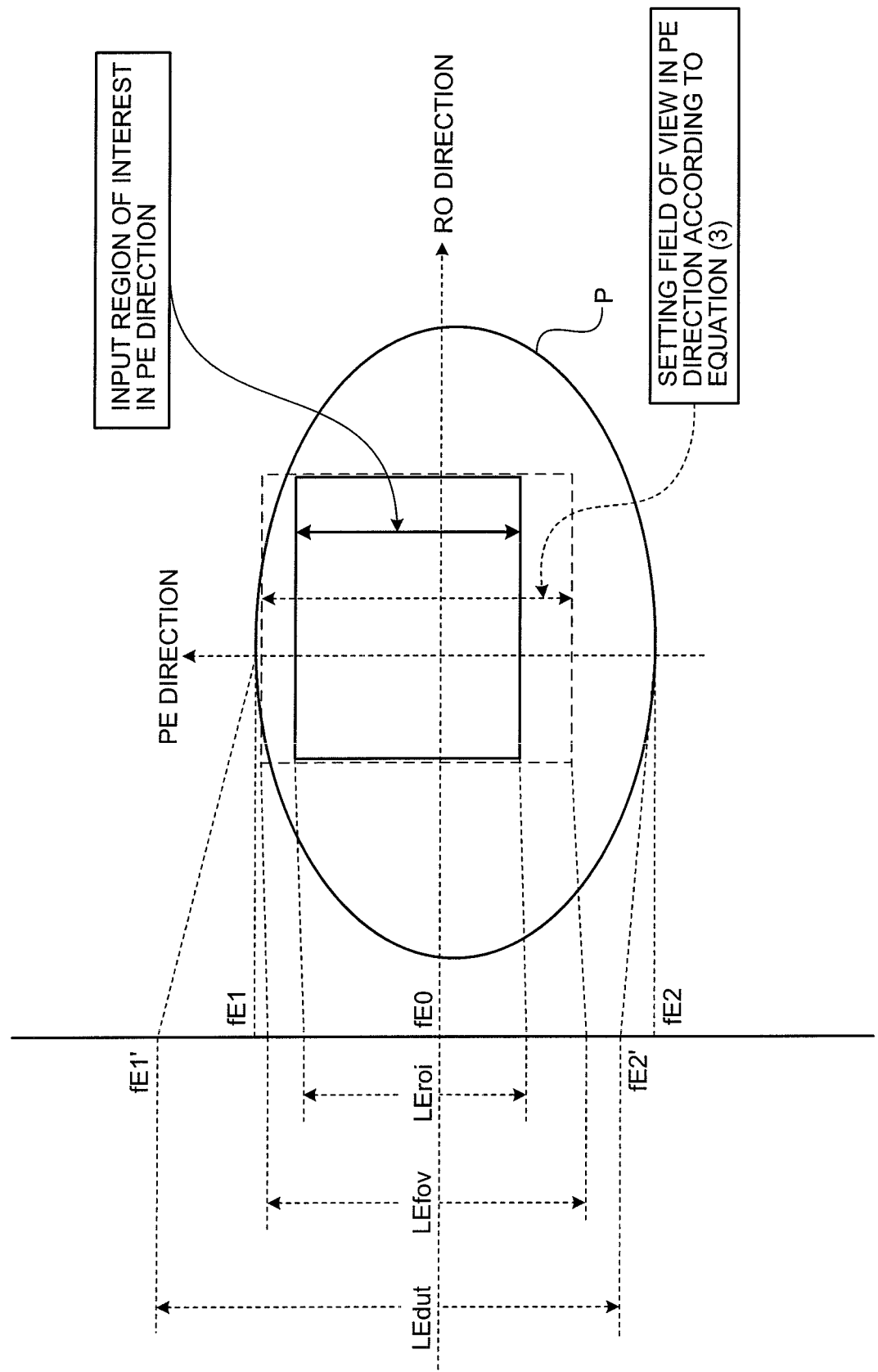
Figure 9:
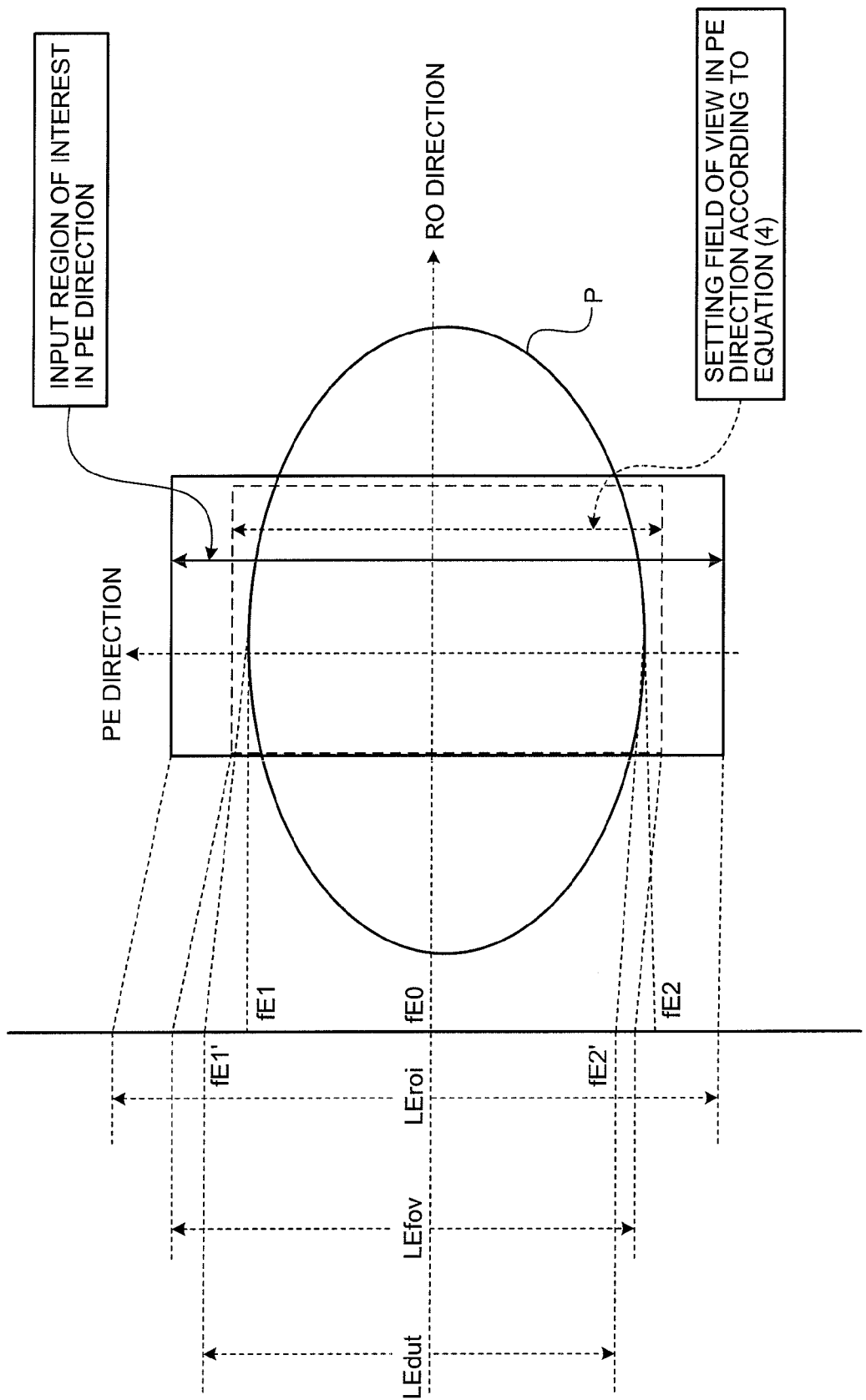
Figure 10:
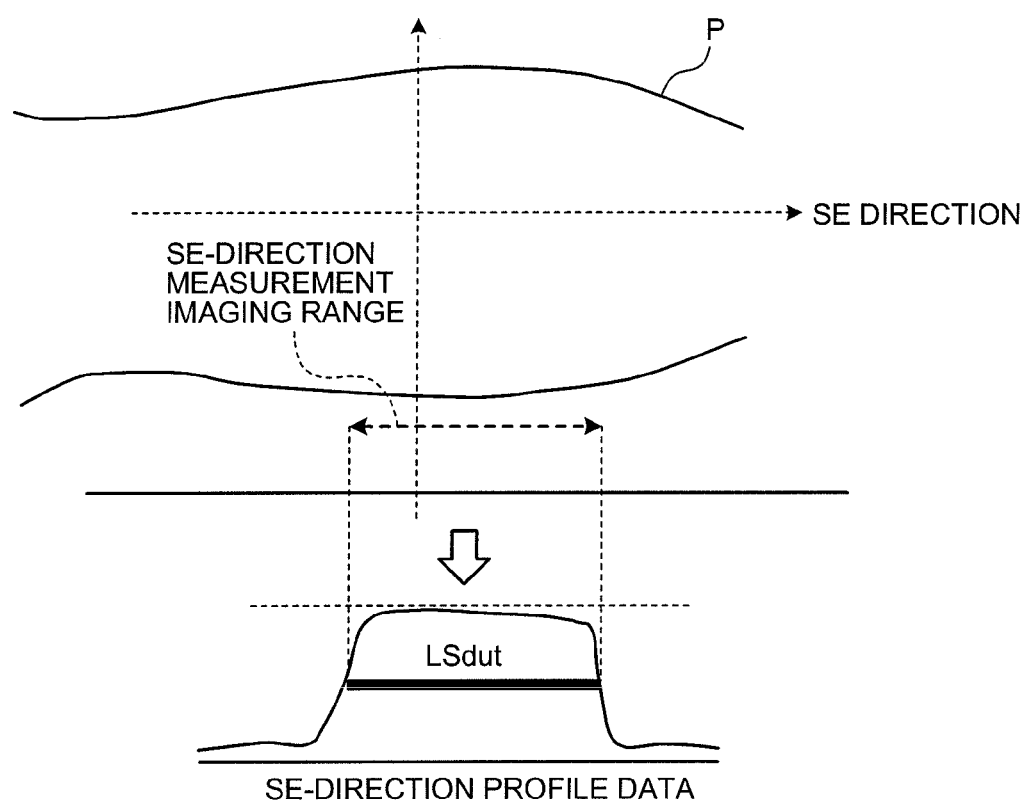
FIGS. 10 and 11 are diagrams for explaining the setting of the field of view in the SE direction.
Figure 11:
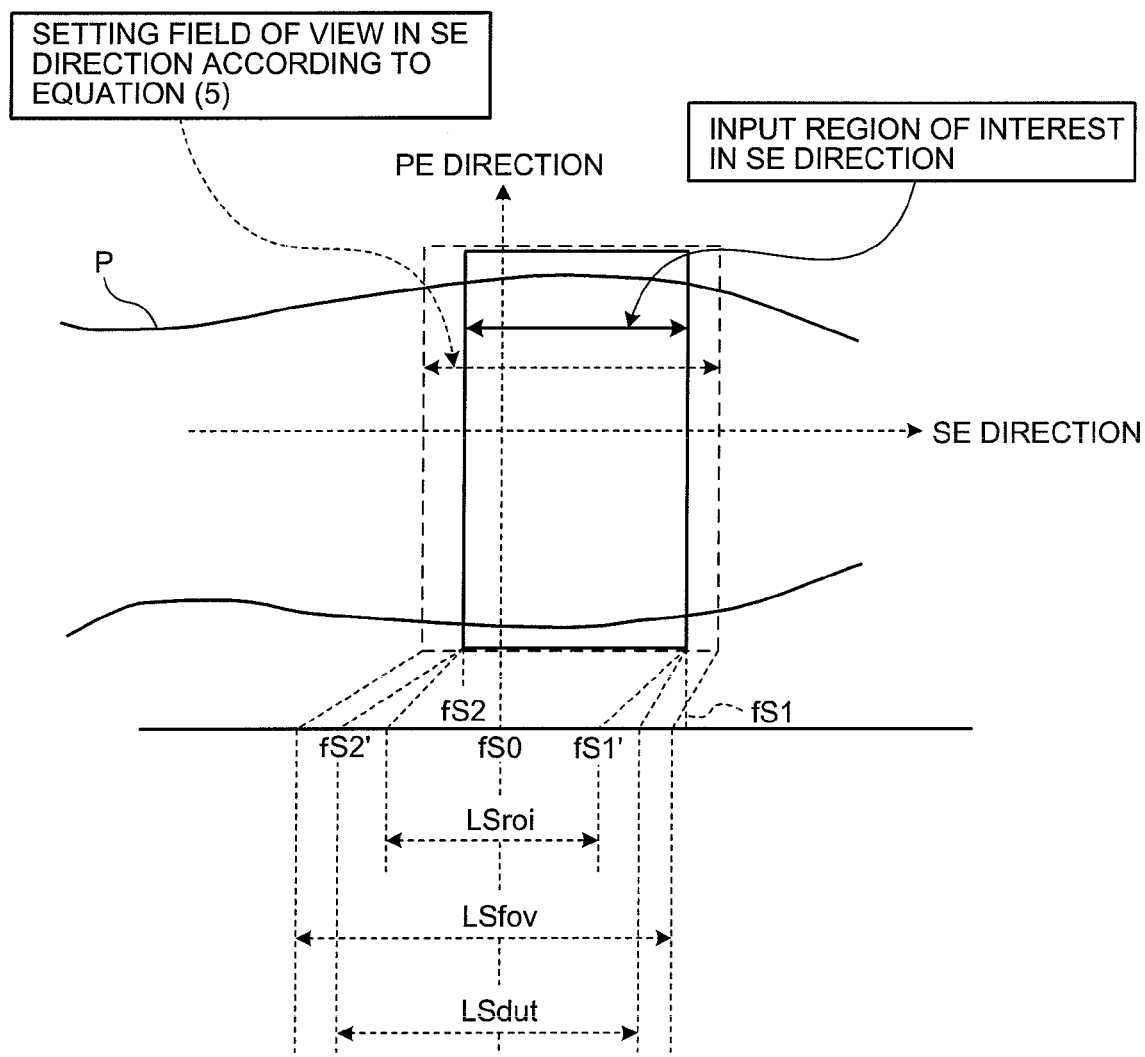

The feature of the MRI apparatus 100 according to the present embodiment resides in that the later-described control unit 17 can easily set a field of view that prevents aliasing artifacts from occurring when taking a magnetic resonance image. This feature is now explained with reference to FIGS. 2 to 11. FIG. 2 is a diagram for explaining a configuration of a control unit according to the embodiment, and FIG. 3 is a diagram for explaining a region of interest. FIGS. 4 to 6 are diagrams for explaining the setting of the field of view in the RO direction, FIGS. 7 to 9 are diagrams for explaining the setting of the field of view in the PE direction, and FIGS. 10 and 11 are diagrams for explaining the setting of the field of view in the SE direction.

In the following explanation, it is assumed that the MRI apparatus 100 takes a three-dimensional magnetic resonance image.

As illustrated in FIG. 2, the control unit 17 according to the present embodiment includes a measurement data acquisition control unit 17a and the field-of-view setting unit 17b as components closely related to the present invention.

The measurement data acquisition control unit 17a performs control in such a manner that data for measuring the dimensions of the subject P in the RO, PE, and SE directions is acquired, based on the information on the region of interest received from the operator who is referring to the positioning images by way of the input unit 16 at the time of planning the positioning.

First, the operator establishes the three-dimensional region of interest at the time of planning the positioning, as illustrated in FIG. 3, for example. At this time, the operator also determines the RO, PE, and SE directions in the three-dimensional region of interest. Or, the MRI apparatus 100 may automatically determine these encoding directions. The measurement data acquisition control unit 17a thereby acquires "the RO, PE, and SE directions of the region of interest" necessary to take an image of the subject P.

The size of the region of interest established by the operator (more specifically, the frequency information as positional information) and the encoding directions (the RO, PE, and SE directions) are sent to the field-of-view setting unit 17b, which is described later.

Then, the measurement data acquisition control unit 17a performs the following controlling process to acquire profile data for measuring the dimensions of the subject P in the established encoding directions. In particular, the measurement data acquisition control unit 17a controls the gradient magnetic field power source 3, the transmitting unit 7, the receiving unit 9, the data collecting unit 12, and the data processing unit 13 by way of the interface unit 11, in such a way as to selectively excite all the slices in the predetermined field of view by high-frequency pulses and to generate profile data projected in the encoding directions from the k-space data of the collected magnetic resonance signal data. The measurement data acquisition control unit 17a sets the field of view (imaging range for each item of the profile data) that has an area large enough for the size of the subject P (for example, the maximum area in which the reception RF coil 8 can receive a magnetic resonance signal).

In FIG. 2, the field-of-view setting unit 17b sets the field of view, based on the dimensions of the subject in the encoding directions and the dimensions of the region of interest in the encoding directions. More specifically, the field-of-view setting unit 17b sets the field of view, based on the relationship between the dimension of the subject in each encoding direction and the dimension of the region of interest in each encoding direction. In particular, the field-of-view setting unit 17b sets the field of view, in accordance with the positional information of the region of interest in each encoding direction received from the input unit 16 and also with the relationship between the dimension in each encoding direction of the subject that is determined from the profile data of the subject P generated for each encoding direction by the data processing unit 13 under the control by the measurement data acquisition control unit 17a and the dimension of the region of interest. In the following explanation, the process of setting the field of view that is performed for each encoding direction by the field-of-view setting unit 17b will be explained in the order of the RO, PE, and SE directions.

When the field of view is to be set in the RO direction, the field-of-view setting unit 17b calculates, as illustrated in FIG. 4, the half width LRdut of the RO-direction profile data in the RO-direction measurement imaging range. Then, the field-of-view setting unit 17b determines the obtained LRdut as a value corresponding to the dimension of the subject P in the RO direction.

When the maximum RO-direction frequency of the subject P in all the slices that are subjected to the selective excitation is fR1 and the minimum RO-direction frequency of the subject P in all the slices that are subjected to the selective excitation is fR2, the field-of-view setting unit 17b sets LRdut to fR1-fR2. In addition, when the RO-direction center frequency of the region of interest is fRO, the field-of-view setting unit 17b determines fR1 and fR2 as fR1' and fR2' with reference to fRO. The field-of-view setting unit 17b also calculates the value LRroi, which is the dimension of the region of interest in the RO direction, based on the frequency information of the region of interest in the RO direction.

As illustrated in FIG. 5, when the subject P is larger in the RO direction than the region of interest, the field-of-view setting unit 17b calculates the field of view in the RO direction (LRfov) by use of LRdut and LRroi according to the following equation (1) in such a manner that the aliasing region of the subject P in the RO direction outside the region of interest would not overlie the region of interest. The coefficients $\alpha_r$ and $\beta_r$ of the equation (1) are pre-stored in a coefficient storage unit 14a shown in FIG. 2.

$$LRfov=((LRdut+LRroi)/2)*\alpha_r+\beta_r \quad (1)$$

On the other hand, as illustrated in FIG. 6, when the subject P is smaller in the RO direction than the region of interest, the field-of-view setting unit 17b determines that the frequency area higher than fR1' and the frequency area lower than fR2' are unnecessary areas, and calculates the field of view in the RO direction (LRfov) according to the following equation (2) by use of LRdut. The coefficients $\alpha_r$ and $\beta_r$ are the same as those of the equation (1), but the coefficients of the equation (2) may be different from those of the equation (1).

$$LRfov=LRdut*\alpha_r+\beta_r \quad (2)$$

Next, when the field of view is to be set in the PE direction, the field-of-view setting unit 17b calculates the half width LEdut for the PE-direction profile data in the PE-direction measurement imaging range, as illustrated in FIG. 7. Then, the field-of-view setting unit 17b determines the obtained LEdut as the value corresponding to the dimension of the subject P in the PE direction.

When the maximum PE-direction frequency of the subject P in all the slices that are subjected to the selective excitation is fE1 and the minimum PE-direction frequency of the subject P in all the slices that are subjected to the selective excitation is fE2, the field-of-view setting unit 17b sets LEdut to fE1-fE2. Furthermore, when the center frequency of the region of interest in the PE direction is fEO, the field-of-view setting unit 17b determines fE1 and fE2 as fE1' and fE2' with reference to fE0. The field-of-view setting unit 17b also calculates LEroi, which is the dimension of the region of interest in the PE direction, based on the frequency of the region of interest in the PE direction.

Then, when the subject P is larger in the PE direction than the region of interest, the field-of-view setting unit 17b calculates, as illustrated in FIG. 8, the field of view of the PE direction (LEfov) by use of LEdut and LEroi according to the following equation (3) in such a manner that the aliasing region of the subject P outside the region of interest in the PE direction would not overlie the region of interest. The coefficients $\alpha_e$ and $\beta_e$ in the equation (3) are pre-stored in the coefficient storage unit 14a shown in FIG. 2.

$$LEfov=((LEdut+LEroi)/2)*\alpha_e+\beta_e \quad (3)$$

On the other hand, when the subject P is smaller in the PE direction than the region of interest as illustrated in FIG. 9, the field-of-view setting unit 17b determines the frequency area higher than fE1' and a frequency area lower than fE2' as unnecessary areas and calculates the field of view in the PE direction (LEfov) by use of LEdut according to the following equation (4). The coefficients $\alpha_e$ and $\beta_e$ of the equation (4) are the same as those of the equation (3), but the coefficients of the equation (4) may be different from those of the equation (3).

$$LEfov=LEdut*\alpha_e+\beta_e \quad (4)$$

Next, when the field of view is to be set in the SE direction, the field-of-view setting unit 17b calculates the half width LSdut of the SE-direction profile data in the SE-direction measurement imaging range, as illustrated in FIG. 10. Then, the field-of-view setting unit 17b determines the obtained LSdut as the value corresponding to the dimension of the subject P in the SE direction.

When the maximum SE-direction frequency of the subject P in all the slices that are subjected to the selective excitation is fS1 and the minimum PE-direction frequency of the subject P in all the slices that are subjected to the selective excitation is fS2, the field-of-view setting unit 17b sets LSdut to fS1-fS2. Furthermore, when the center frequency of the region of interest in the SE direction is fSO, the field-of-view setting unit 17b determines fS1 and fS2 as fS1' and fS2' with reference to fSO. The field-of-view setting unit 17b also calculates LSroi, which is the dimension of the region of interest in the SE direction, from the frequency of the region of interest in the SE direction.

If satisfactory selective excitation properties cannot be attained in the imaging region in the SE direction, aliasing artifacts tend to appear also in the slice direction. For this reason, the field-of-view setting unit 17b calculates, as illustrated in FIG. 11, the field of view in the SE direction (LSfov) by use of LSdut according to the equation (5), regardless of the size relationship between the subject P and the region of interest in the SE direction. The coefficients $\alpha_s$ and $\beta_s$ of the equation (5) are pre-stored in the coefficient storage unit 14a of FIG. 2.

$$LSfov=LSdut*\alpha_s+\beta_s \quad (5)$$

In this manner, the field-of-view setting unit 17b sets the field of view in the RO, PE, and SE directions for taking a three-dimensional magnetic resonance image. Then, the field-of-view setting unit 17b generates a pulse sequence, based on the set field of view, and sends the generated pulse sequence by way of the interface unit 11 to the gradient magnetic field power source 3, the transmitting unit 7, and the receiving unit 9 so that the imaging of the three-dimensional magnetic resonance image is executed.

In the above explanation, the profile data of each encoding direction is generated after the setting of the region of interest is received, and then the size of the subject P is measured from the half widths of the generated profile data. The present invention is not limited thereto, however. For example, sensitivity map data of an array coil that is used in parallel imaging or the like may be adopted. In other words, the field-of-view setting unit 17b generates profile data of each encoding direction for the region of interest that is set at the time of planning the positioning from the sensitivity map data that is obtained in advance, and the half width of the generated profile data is determined as a value that corresponds to the dimension of the subject P in the corresponding encoding direction.

When the MRI apparatus 100 takes a two-dimensional magnetic resonance image, the field-of-view setting unit 17b sets the field of view in the RO and PE directions.

Figure 12:
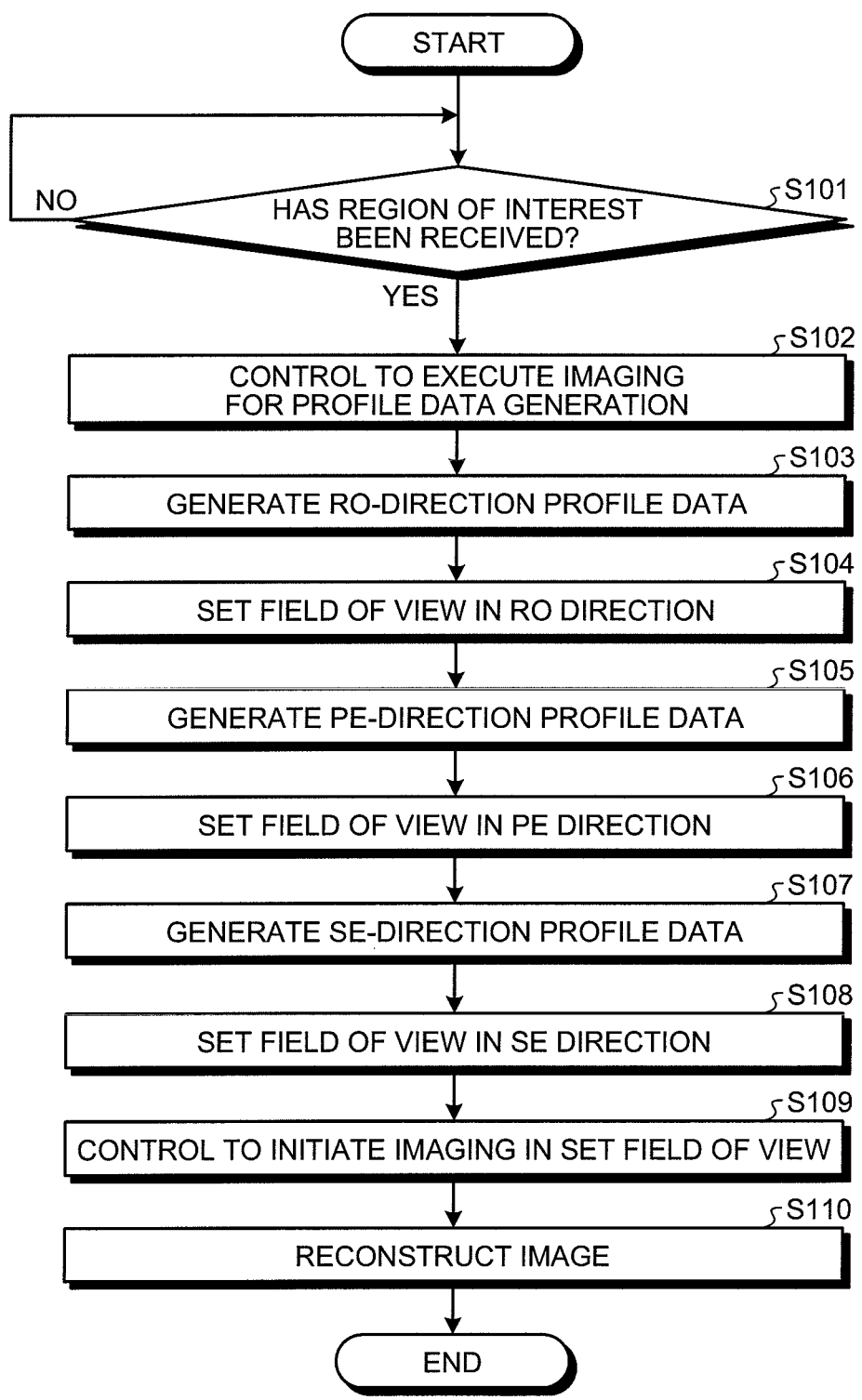
FIG. 12 is a diagram for explaining a process performed by the MRI apparatus according to the embodiment.

The procedure of the process performed by the MRI apparatus 100 according to the present embodiment is now explained with reference to FIG. 12. FIG. 12 is a diagram for explaining a process performed by the MRI apparatus according to the embodiment.

As illustrated in FIG. 12, when the MRI apparatus 100 according to the present embodiment receives the setting of the region of interest from the operator (yes at step S101), the measurement data acquisition control unit 17a performs controls so that an image for profile data generation is taken (step S102).

In particular, the measurement data acquisition control unit 17a controls the gradient magnetic field power source 3, the transmitting unit 7, the receiving unit 9, and the data collecting unit 12 by way of the interface unit 11 in such a way as to selectively excite all the slices in the predetermined field of view by high-frequency pulses and to generate profile data projected in the encoding directions from the k-space data of the collected magnetic resonance signal data.

Then, the data processing unit 13 generates the RO-direction profile data (step S103), and the field-of-view setting unit 17b sets the field of view in the RO direction by use of the coefficient for the RO direction that is stored in the coefficient storage unit 14a, based on the relationship of the dimension of the subject P calculated from the RO-direction profile data and the dimension of the region of interest in the RO direction (step S104, see FIGS. 4 to 6 and Equations (1) and (2)).

Thereafter, the data processing unit 13 generates the PE-direction profile data (step S105), and the field-of-view setting unit 17b sets the field of view in the PE direction, based on the relationship between the dimension of the subject P calculated from the PE-direction profile data and the dimension of the region of interest in the PE direction, by use of the coefficient for the PE direction that is stored in the coefficient storage unit 14a (step S106, see FIGS. 7 to 9 and Equations (3) and (4)).

Then, the data processing unit 13 generates the SE-direction profile data (step S107), and the field-of-view setting unit 17b sets the field of view in the SE direction by use of the coefficient for the SE direction that is stored in the coefficient storage unit 14a, based on the dimension of the subject P calculated from the SE-direction profile data (step S108, see FIGS. 10 and 11 and Equation (5)).

The field-of-view setting unit 17b controls the gradient magnetic field power source 3, the transmitting unit 7, and the receiving unit 9 by way of the interface unit 11 so that an image-taking operation is initiated in the set field of view (step S109).

Thereafter, the data processing unit 13 reconstructs a three-dimensional magnetic resonance image from the k-space data (step S110), and terminates the process.

The order of setting the field of view may be arbitrarily changed. In addition, the profile data for the encoding directions may be generated altogether, after step S102 of FIG. 12.

As described above, according to the present embodiment, when the setting of the region of interest is received from the operator, the measurement data acquisition control unit 17a performs control so that an image for generating profile data is taken. The data processing unit 13 generates the profile data for each encoding direction of the region of interest. Then, the field-of-view setting unit 17b sets the field of view for each encoding direction by use of the coefficients stored in the coefficient storage unit 14a, based on the relationship between the dimensions of the subject P calculated from the profile data for each encoding direction and the dimensions of the region of interest in the corresponding encoding direction.

According to the present embodiment, even when the subject is larger than the region of interest, an optimal field of view free of aliasing artifacts can be automatically set, once the operator makes the setting of the region of interest. Thus, as set forth above, the apparatus according to the present embodiment can readily set the field of view that avoids any aliasing artifacts. Moreover, when the subject is smaller than the region of interest, the coefficients for calculating the field of view are adjusted so that unnecessary data would not be collected. Thus, the load of the system in the reconstruction calculating process and the like can be reduced, and the stability of the system of the MRI apparatus 100 can be improved.

According to the present embodiment, the field-of-view setting unit 17b sets the field of view in each encoding direction, but the present invention is not limited thereto. The field-of-view setting unit 17b may set the field of view only in an encoding direction that is designated by the operator.

For example, an aliasing artifact that appears in the RO direction can be avoided by oversampling a magnetic resonance signal which can be realized without extending the imaging time, or by filtering. Thus, the operator may issue an instruction that the field-of-view setting unit 17b automatically sets the field of view only in the PE direction that is more susceptible to aliasing artifacts. In addition, for the RO direction that is not set through the process using the above Equations (1) and (2) by the field-of-view setting unit 17b, the operator may manually adjust and set the field of view, or the region of interest set by the field-of-view setting unit 17b may be directly adopted as the field of view.

Figure 13:
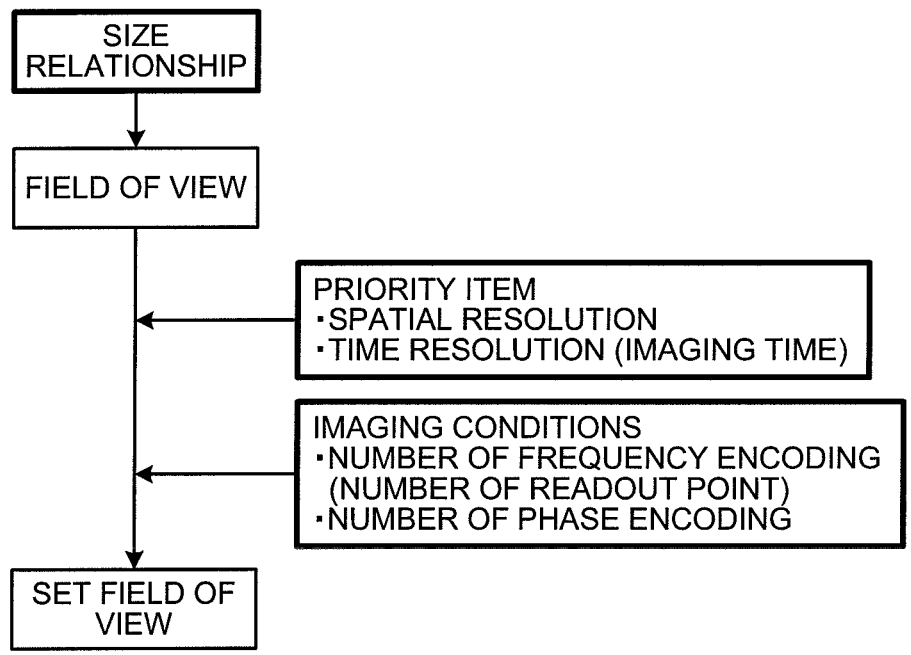
FIGS. 13 and 14 are diagrams for explaining modified examples of fields of view that are set by the field-of-view setting unit.
Figure 14:
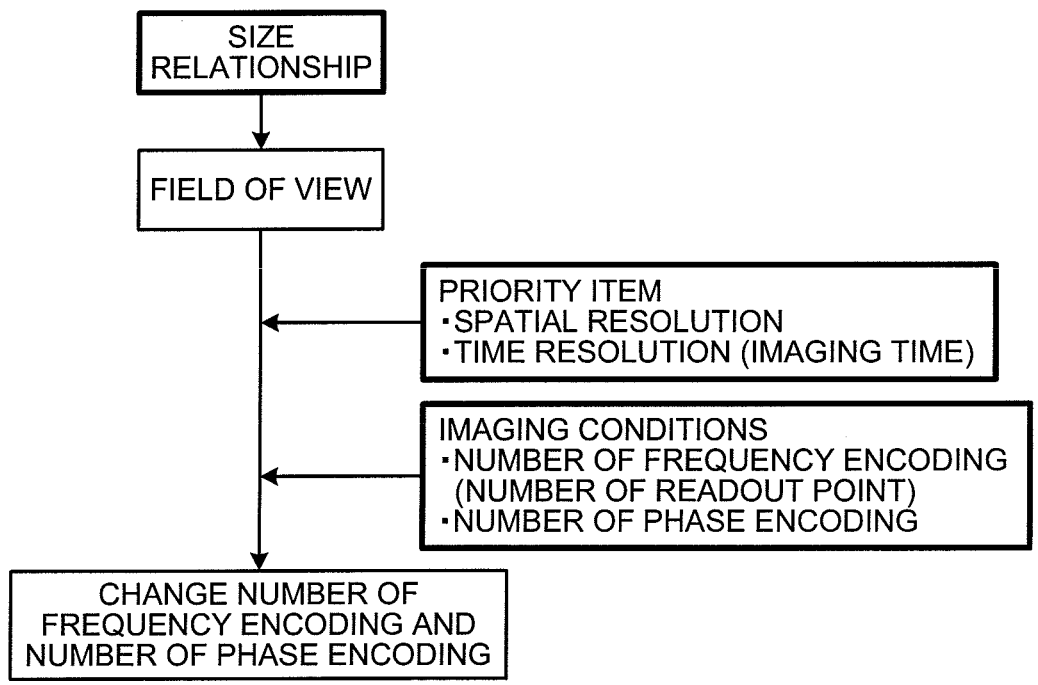

According to the present embodiment, the field-of-view setting unit 17b sets the field of view based on relationship between the dimension of the subject in each encoding direction and the dimension of the region of interest, but the present invention is not limited thereto. More specifically, the field-of-view setting unit 17b of the present invention may set the field of view for taking a magnetic resonance image in which either time resolution or spatial resolution is given a higher priority, based on the dimension of the subject in each encoding direction and the dimension of the region of interest. FIGS. 13 and 14 are diagrams for explaining modification examples of the fields of view set by the field-of-view setting unit.

More specifically, the field-of-view setting unit 17b sets the field of view, based on the size relationship and also on a priority item indicating which of the time resolution (imaging time) and the spatial resolution of the taken magnetic resonance image should be given a higher priority, and on imaging conditions such as the number of frequency encoding and the number of phase encoding, as illustrated in FIG. 13.

Here, the imaging conditions for the magnetic resonance image that are provided by the operator include the number of frequency encoding and the number of phase encoding. When a three-dimensional image is taken, the number of slice encoding is also included. The number of frequency encoding is provided as the number of readout point among the imaging conditions, as illustrated in FIG. 13. The time resolution (imaging time) of the taken magnetic resonance image is dependent on the number of phase encoding. When a three-dimensional image is taken, the time resolution (imaging time) of the taken magnetic resonance image is dependent on the number of phase encoding and the number of slice encoding. On the other hand, the spatial resolution of the taken magnetic resonance image is dependent on the product of the maximum intensity of the gradient magnetic field and the application time in the phase encoding. Moreover, when a three-dimensional image is taken, the spatial resolution of the target magnetic resonance image is dependent on the product of the maximum intensity of the gradient magnetic field and the application time in the phase encoding and on the product of the maximum intensity of the gradient magnetic field and the application time in the slice encoding. To widen the field of view is to reduce the increment of the product of the intensity of the gradient magnetic field and the application time. To reduce the field of view is to increase the increment of the product of the intensity of the gradient magnetic field and the application time.

The operator of the MRI apparatus 100 therefore determines the priority item indicating which of the time resolution and the spatial resolution should be given a priority, through the input unit 16 at the time of setting the region of interest. The field-of-view setting unit 17b sets the field of view, based on the size relationship in the same manner as in the first embodiment. For example, when the subject P is smaller in the PE direction than the region of interest, as illustrated in FIG. 9, the field-of-view setting unit 17b calculates the field of view in the PE direction that is smaller in the PE direction than the region of interest, according to the Equation (4). Then, as illustrated in FIG. 13, the field-of-view setting unit 17b sets the calculated field of view in the PE direction, based on the priority item and the imaging conditions.

For example, when the time resolution is selected as the priority item, and when the subject P is smaller than the region of interest, the increment of the product of the intensity of the gradient magnetic field and the application time can be set to a large value. Thus, the field-of-view setting unit 17b reduces the number of encoding, while maintaining the product of the maximum intensity of the gradient magnetic field and the application time. As a result, the imaging time can be reduced. When the spatial resolution is selected as the priority item, and when the subject P is smaller than the region of interest, the field-of-view setting unit 17b increases the product of the maximum intensity of the gradient magnetic field and the application time, without changing the number of encoding. As a result, the spatial resolution can be improved.

Alternatively, as illustrated in FIG. 14, the field-of-view setting unit 17b changes the preset imaging conditions including the number of frequency encoding and the number of phase encoding to the imaging conditions including the number of frequency encoding and the number of phase encoding for taking a magnetic resonance image in the field of view that is set based on the size relationship, in accordance with the priority item. For example, when the subject P is smaller than the region of interest, the field-of-view can be reduced in a manner that aliasing artifacts do not generate. That is, the increment of the product of the intensity of the gradient magnetic field and the application time can be increased. So, when the time resolution is selected as the priority item, the field-of-view setting unit 17b reduces the number of phase encoding so as to maintain the product of the maximum intensity of the gradient magnetic field and the application time. As a result, the imaging time can be reduced. And, when the spatial resolution is selected as the priority item, the field-of-view setting unit 17b increases the product of the maximum intensity of the gradient magnetic field and the application time by maintaining the number of phase encoding. As a result, the spatial resolution can be improved.

On the other hand, when the subject P is larger than region of interest, the field-of-view must be widened to avoid generating aliasing artifacts. That is, the increment of the product of the intensity of the gradient magnetic field and the application time must be reduced. So, when the time resolution is selected as the priority item, the field-of-view setting unit 17b maintains the number of phase encoding. As a result, the spatial resolution is lowering because of reducing the product of the maximum intensity of the gradient magnetic field and the application time, but the time resolution is maintained. And, when the spatial resolution is selected as the priority item, the field-of-view setting unit 17b increases the number of phase encoding so as to maintain the product of the maximum intensity of the gradient magnetic field and the application time. As a result, the time resolution is increased, but the spatial resolution is maintained.

With the above process, the field-of-view setting unit 17b determines the field of view and the imaging conditions for taking a magnetic resonance image in accordance with the priority item, and the control unit 17 thereby generates pulse sequence information based on the determined field of view and imaging conditions.

The priority item may be selected manually by the operator each time a magnetic resonance image is taken, or default settings may be provided in the MRI apparatus 100. Alternatively, the priority item may be preset for each imaging region. For example, the operator may preset "spatial resolution" for the priority item if the imaging region is "brain", which requires a detailed image analysis, while presetting "time resolution" if the imaging region is "heart", which is associated with motions. Then, the field-of-view setting unit 17b uses the priority item preset for the target imaging region to perform the process explained with reference to FIG. 13 or 14.

Figure 15:
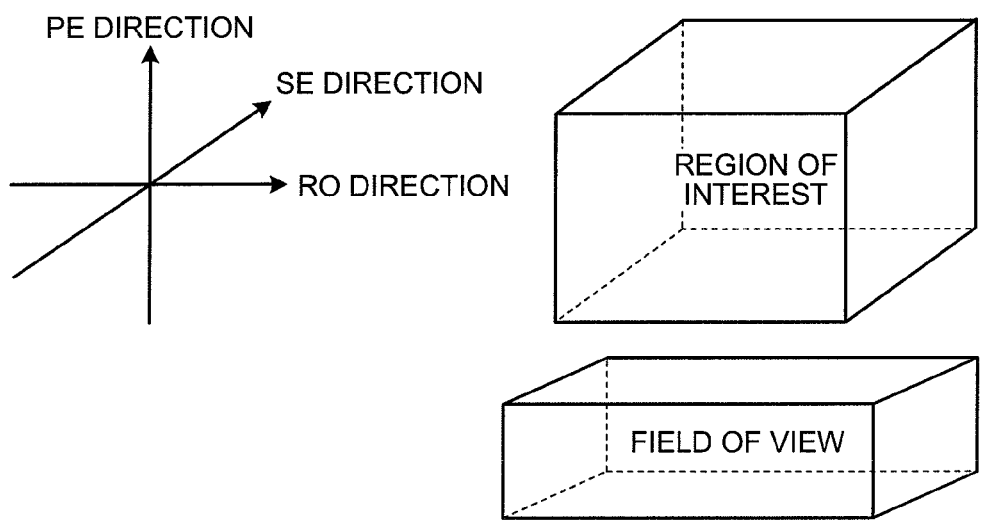
FIG. 15 is a diagram for explaining display control conducted by the control unit.

In addition, the present invention may present the field of view set by the field-of-view setting unit 17b to the operator and leaves to the operator the judgment as to whether the field of view set by the field-of-view setting unit 17b should be used or should be adjusted before being used. More specifically, the control unit 17 controls the display unit 15 to display the field of view set by the field-of-view setting unit 17b on the monitor of the display unit 15. FIG. 15 is a diagram for explaining display control conducted by the control unit For example, the control unit 17 controls the display unit 15 to display the field of view set by the field-of-view setting unit 17b along with the information of the encoding directions and the region of interest on the monitor of the display unit 15, as illustrated in FIG. 15. Then, the operator judges whether the automatically set field of view should be used for imaging without making any changes or a field of view obtained by adjusting the automatically set field of view should be used for imaging. The control unit 17 may control the data processing unit 13 to generate a sample image of the magnetic resonance image taken in the set field of view and display it on the monitor, instead of displaying the field of view. For example, the data processing unit 13 may generate the sample image from the data used when reconstructing a positioning image.

Figure 16:
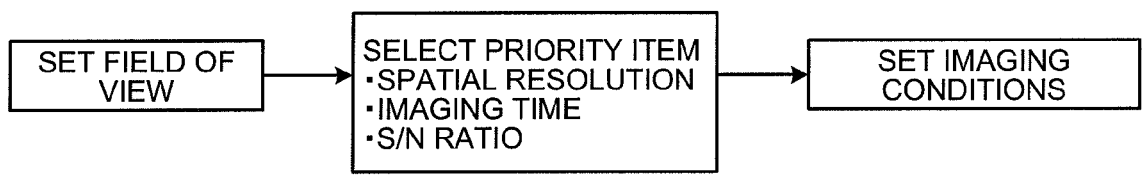
FIG. 16 is a diagram for explaining the first modified example.
Figure 17:
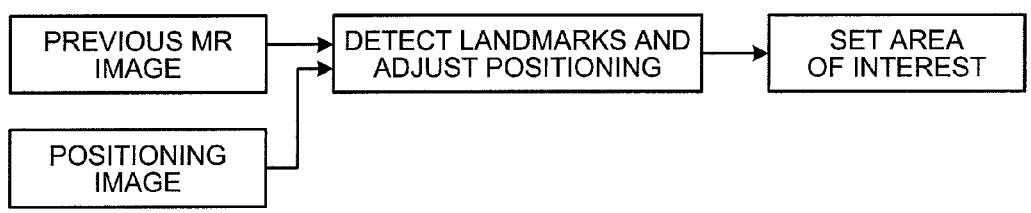
FIG. 17 is a diagram for explaining the second modified example.
Figure 18:
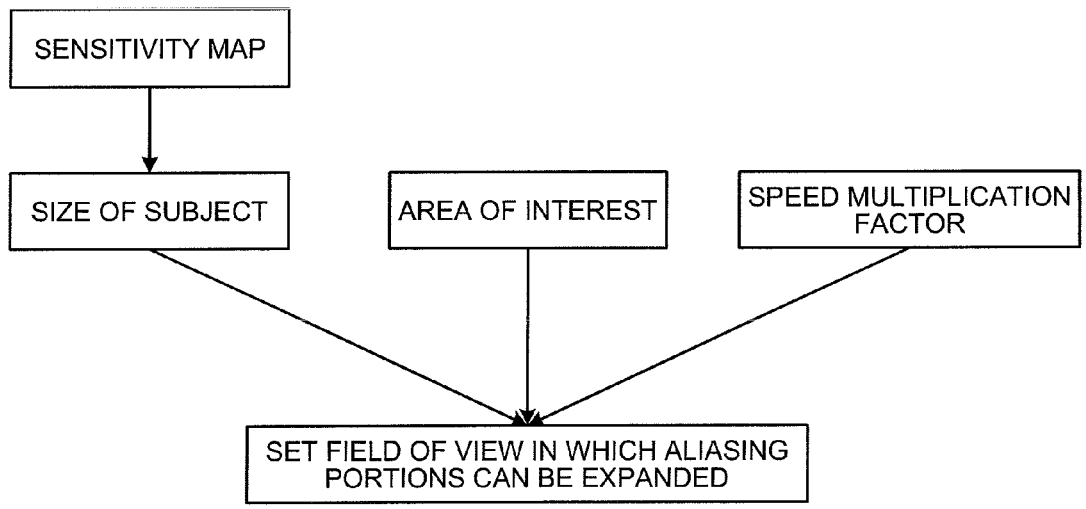
FIG. 18 is a diagram for explaining the third modified example.

The present invention may be realized in various other modifications than the above embodiment. In the following explanation, other modification examples of the present invention are discussed with reference to FIGS. 16 to 18. FIG. 16 is a diagram for explaining the first modification example, FIG. 17 is a diagram for explaining the second modification example, and FIG. 18 is a diagram for explaining the third modification example.

According to the first modification example, when taking an image of the subject P in the set field of view, the field-of-view setting unit 17b performs control in such a manner that the imaging conditions are changed, based on the priority item received from the operator indicating which one of the spatial resolution, the imaging time, and the signal/noise ratio should be given a priority, as illustrated in FIG. 16.

When the field-of-view setting unit 17b makes changes to the default field of view and sets the field of view, the operator needs to suitably adjust the imaging matrix and the number of acquisition to stabilize the spatial resolution and the signal/noise ratio. The imaging matrix and the number of additions with respect to the PE direction (the SE direction is also included when taking a three-dimensional image) are dependent on the imaging time. If the imaging matrix and the number of acquisition are adjusted in such a manner to preferentially stabilize the spatial resolution or the signal/noise ratio, the imaging time is adversely extended. For this reason, the operator needs to have the MRI apparatus 100 execute imaging of the magnetic resonance image in the set field of view, in consideration of the spatial resolution, the signal/noise ratio, and the imaging time.

For example, when the operator, who is notified on the screen of the display unit 15 of the field of view being larger than the default field of view, selects the spatial resolution in the PE and SE directions as a priority item, the field-of-view setting unit 17b performs control for executing image-taking in such a manner that a pulse sequence is generated by which the imaging time is increased and the signal/noise ratio is lowering, but the spatial resolution can be maintained.

Furthermore, when the operator, who is notified on the screen of the display unit 15 of the field of view being larger than the default field of view, selects the imaging time as a priority item, the field-of-view setting unit 17b performs control in such a manner that a pulse sequence is generated by which the signal/noise ratio is lowering, but the imaging time can be maintained.

When the operator, who is notified on the screen of the display unit 15 of the field of view being larger than the default field of view, selects the signal/noise ratio in the PE and SE directions as a priority item, the field-of-view setting unit 17b performs control in such a manner that a pulse sequence is generated by which the time resolution is lowering, but the signal/noise ratio of an image that can be maintained.

In this manner, a magnetic resonance image free of aliasing artifacts can be taken in accordance with the priority item selected by the operator.

According to the second modification example, the region of interest is not set manually by the operator, but the region of interest is automatically set, based on the information preset for different imaging regions.

More specifically, according to the second modification example, when taking an image of a region of the subject for which a magnetic resonance image has been taken in the past, the imaging region of the previous magnetic resonance image is adopted as the region of interest. Then, the dimension of the subject P is measured for each encoding direction of this region of interest to set the field of view.

In particular, when taking an image of the same region (e.g., abdomen) of the same subject as the previous image, the measurement data acquisition control unit 17a detects landmarks from the previous magnetic resonance image and the positioning image and performs position adjustment. The imaging region of the previous magnetic resonance image can thereby be adopted for the region of interest for taking the new image, as illustrated in FIG. 17.

Then, the measurement data acquisition control unit 17a performs control in such a manner that the encoding directions in the imaging region of the previous magnetic resonance image are adopted for the set region of interest to take the new profile data generating image. The field-of-view setting unit 17b sets the field of view from the profile data and the region of interest set by the measurement data acquisition control unit 17a. In this manner, even when the size of the same region of the subject has been changed in accordance with the gained weight of the subject, the field of view free of aliasing artifacts can be set.

Alternatively, according to the second modification example, instead of a previously taken magnetic resonance image, three-dimensional positional information of standard landmarks for different imaging regions (standard landmark three-dimensional positional information) may be pre-stored together with the encoding directions, and the measurement data acquisition control unit 17a sets the region of interest based on the standard landmark three-dimensional positional information. In other words, the measurement data acquisition control unit 17a performs position adjustment by comparing the positional information of the landmarks detected from a new positioning image of the subject P with the standard landmark three-dimensional positional information to set a new region of interest of the subject P.

According to the third modification example, when taking a magnetic resonance image by parallel imaging, the field-of-view setting unit 17b sets the field of view, based on the dimensions of the subject in the encoding directions, the dimensions of the region of interest in the corresponding encoding directions, and the speed multiplication factor determined in the parallel imaging.

More specifically, in the parallel imaging as illustrated in FIG. 18, the field-of-view setting unit 17b generates profile data from the sensitivity map data of the array coil obtained at the time of planning the positioning and calculates the size of the subject. Then, as illustrated in FIG. 18, the field-of-view setting unit 17b sets the field of view in which aliasing portions can be expanded, based on the size of the subject, the region of interest input by the operator, and the speed multiplication factor, which is a parameter of the parallel imaging. Thus, the field of view free of aliasing artifacts can be set also in parallel imaging.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus, comprising:
   an acquiring unit acquires a size dimension data profile of the subject in each of one or more encoding directions selectively set in a region of interest (ROI) that is received from an operator; and
   a field-of-view (FOV) setting unit that compares the size dimension(s) in the data profile of the subject acquired in each of the one or more selectively set encoding directions, by the acquiring unit, with the corresponding size dimension(s) of the ROI, occurring in each of the one or more selectively set encoding directions, in order to obtain a comparison result; and the FOV setting unit, making use of the obtained comparison result, between the size dimensions of the subject in each of the one or more selectively set encoding directions, and the corresponding size dimension(s) of the ROI, in order to select/choose, based on that obtained comparison result, at the start of a magnetic resonance imaging scan, a single FOV setting that permits both a minimized/shortened magnetic resonance imaging scan time in combination with the acquisition of an aliasing-free/artifact-reduced magnetic resonance image.

2. The magnetic resonance imaging apparatus according to claim 1, wherein, when the size dimension(s) of the subject in each of the one or more selectively set encoding directions acquired by the acquiring unit is larger than the dimension of the region of interest in each of the one or more selectively set encoding directions, the field-of-view setting unit sets the field of view in such a manner that the area of the subject that is outside the region of interest and is folded back would not overlay or cause aliasing of the region of interest.

3. The magnetic resonance imaging apparatus according to claim 1, wherein the field-of-view setting unit sets the field of view, based on the size relationship comparison, and also on a priority item indicating which of a time resolution and a spatial resolution is to be given a priority in determining the imaging conditions of the magnetic resonance image that is to be obtained.

4. The magnetic resonance imaging apparatus according to claim 3, wherein the field-of-view setting unit changes said imaging conditions adopted in acquiring the magnetic resonance image in the field of view set based on the size relationship, in accordance with the priority item indicating the chosen selection of which of a time resolution and a spatial resolution of the magnetic resonance image, is considered as having priority, with respect to the magnetic resonance image being acquired.

5. The magnetic resonance imaging apparatus according to claim 3, wherein, a priority item is determined within each imaging region to be imaged, with the field of view setting unit then utilizing the particular priority item set, for each respective imaging region on which imaging is to be executed.

6. The magnetic resonance imaging apparatus according to claim 4, wherein, when the priority item is determined within each imaging region of a plurality of imaging regions that comprise the acquired magnetic resonance image, the field of view setting unit sets the field of view, based on the priority item determined for each respective imaging region on which imaging is to be executed.

7. The magnetic resonance imaging apparatus according to claim 1, further comprising: one or more display units and a display control unit that performs control in order to display the field of view set by the field-of-view setting unit on a certain display unit of the one or more displays.

8. The magnetic resonance imaging apparatus according to claim 1, wherein the field of view setting unit sets the field of view only in an encoding direction for which a request, of setting the field of view, is received from the operator.

9. The magnetic resonance imaging apparatus according to claim 1, further comprising an imaging condition control unit that performs control when taking an image of the subject, with the magnetic resonance imaging apparatus, in the field of view set by the field-of-view setting unit, so that an imaging condition is changed in accordance with a selected/chosen priority item received from the operator that indicates which one of the imaging conditions selected from: a spatial resolution, an overall imaging time, and a signal/noise ratio is given priority in performing the magnetic resonance imaging scan.

10. The magnetic resonance imaging apparatus according to claim 1, wherein the acquiring unit sets the region of interest (ROI) of the subject, based on information that has been predetermined for each of a plurality of imaging regions, and acquires the size dimension(s) of the subject in each of the encoding directions that correspond to the plurality of imaging regions that comprise the set ROI region of interest.

11. The magnetic resonance imaging apparatus according to claim 1, wherein, when taking the magnetic resonance image by parallel imaging, the field-of-view setting unit sets the field of view based on the size, dimension(s) of the subject in each of the encoding directions that is acquired by the acquiring unit, the corresponding dimension(s) of the region of interest within each of the encoding directions, and a speed multiplication factor that has been set, in order to carry out the technique of parallel imaging.

12. A magnetic resonance imaging apparatus, comprising:
an acquiring unit acquires a size dimension data profile of the subject in each of one or more encoding directions selectively set in a region of interest (ROI) that is received from an operator; and
a field-of-view (FOV) setting unit that compares the size dimension(s) in the data profile of the subject acquired in each of the one or more selectively set encoding directions, by the acquiring unit, with the corresponding size dimension(s) of the ROI, occurring in each of the one or more selectively set encoding directions, in order to obtain a comparison result in which either one of a time resolution, or a spatial resolution, is given a priority consideration in setting the FOV; and
the FOV setting unit, making use of the obtained comparison result, between the size dimensions of the subject in each of the one or more selectively set encoding directions, and the corresponding size dimension(s) of the ROI, order to select/choose, based on that obtained comparison result, at the start of a magnetic resonance imaging scan, a single FOV setting that is prioritize with respect to the priority consideration along with minimizing/shortening a magnetic resonance imaging scan time in combination with the acquisition of a aliasing-free/artifact-reduced magnetic resonance image.

13. The magnetic resonance imaging apparatus according to claim 12, wherein the field-of-view setting unit sets the field of view, based on the size dimension(s) of the subject in each of the encoding directions and the size dimension(s) of the region of interest in each of the encoding directions, and also on a selected/chosen priority item indicating which of the time resolution or the spatial resolution, is given the priority in the magnetic resonance image that is to be acquired as part of the imaging conditions being utilized by the magnetic resonance imaging apparatus.

14. The magnetic resonance imaging apparatus according to claim 12, wherein the field-of-view setting unit changes the selected/chosen imaging conditions that have been set for acquiring the magnetic resonance image in the field of view that is set, in accordance with a priority item that indicates which of the time resolution or the spatial resolution is to be given priority in the magnetic resonance image that is acquired by the magnetic resonance imaging apparatus.

15. The magnetic resonance imaging apparatus according to claim 12, further comprising: one or more display units and a display control unit that performs control in order to display the field of view set by the field-of-view setting unit on a certain display unit of the one or more displays.

16. The magnetic resonance imaging apparatus according to claim 13, further comprising: one or more display units and a display control unit that performs control in order to display the field of view set by the field-of-view setting unit on a certain display unit of the one or more displays.

17. The magnetic resonance imaging apparatus according to claim 14, further comprising: one or more display units and a display control unit that performs control in order to display the field of view set by the field-of-view setting unit on a certain display unit of the one or more displays.

18. A magnetic resonance imaging apparatus, comprising:
an acquiring unit acquires a size dimension data profile of the subject in each of one or more encoding directions selectively set in a region of interest (ROI) that is received from an operator;
a field-of-view (FOV) setting unit that compares the size dimension(s) in the data profile of the subject acquired in each of the one or more selectively set encoding directions, by the acquiring unit, with the corresponding size dimension(s) of the ROI, occurring in each of the one or more selectively set encoding directions, in order to obtain a comparison result;
one or more display units and a display control unit that performs control in such a manner that the field of view set by the field-of-view setting unit is displayed on a certain display unit of the one or more displays; and
an input unit that receives an operation initiating the adjusting the field of view set by the field-of-view setting unit from the operator, and
the FOV setting unit, making use of the obtained comparison result, between the size dimensions of the subject in each of the one or more selectively set encoding directions, and the corresponding size dimension(s) of the ROI, in order to select/choose, based on that obtained comparison result, at the start of a magnetic resonance imaging scan, a single FOV setting that permits both a minimized/shortened magnetic resonance imaging scan time in combination with the acquisition of an aliasing-free/artifact-reduced magnetic resonance image.

19. The magnetic resonance imaging apparatus according to claim 18, wherein the field-of-view setting unit sets the field of view, based on the size relationship, and also on a selected/chosen priority item that indicates which of the time resolution or the spatial resolution, is given the priority in the magnetic resonance image that is to be acquired as part of the imaging conditions being utilized by the magnetic resonance imaging apparatus.

20. The magnetic resonance imaging apparatus according to claim 18, wherein the field-of-view setting unit changes the selected/chosen imaging conditions that have been adopted for acquiring the magnetic resonance image in the field of view that is set, based on the size relationship, in accordance with a priority item that indicates which of the time resolution or the spatial resolution is to be given priority in the magnetic resonance image that is acquired by the magnetic resonance imaging apparatus.

* * * * *